United States Patent
Li et al.

(10) Patent No.: US 12,017,221 B2
(45) Date of Patent: Jun. 25, 2024

(54) CASCADED DESIGN MICROFLUIDIC STRUCTURE WITH STEP DIFFERENCE

(71) Applicant: National Yang Ming Chiao Tung University, Hsinchu (TW)

(72) Inventors: Bor-Ran Li, Hsinchu (TW); Tzu-Ting Lin, Taipei (TW); Chia-Jen Lee, Wandan Township (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 212 days.

(21) Appl. No.: 17/412,524

(22) Filed: Aug. 26, 2021

(65) Prior Publication Data
US 2022/0062902 A1 Mar. 3, 2022

(30) Foreign Application Priority Data
Aug. 26, 2020 (TW) ................................ 109129199

(51) Int. Cl.
*B01L 3/00* (2006.01)
*G01N 33/49* (2006.01)

(52) U.S. Cl.
CPC ... *B01L 3/502753* (2013.01); *B01L 3/502769* (2013.01); *B01L 2300/0883* (2013.01); *G01N 33/491* (2013.01); *G01N 33/4915* (2013.01)

(58) Field of Classification Search
None
See application file for complete search history.

(56) References Cited

U.S. PATENT DOCUMENTS

| | | | | |
|---|---|---|---|---|
| 8,208,138 B2 * | 6/2012 | Papautsky | .......... | B01D 21/0087 356/336 |
| 2008/0128331 A1 * | 6/2008 | Lean | .......... | B04C 1/00 209/155 |
| 2008/0240987 A1 * | 10/2008 | Yamada | .......... | B01J 19/0093 422/68.1 |
| 2009/0014360 A1 * | 1/2009 | Toner | .......... | C12M 23/16 209/208 |
| 2015/0238963 A1 * | 8/2015 | Han | .......... | B03B 5/62 210/801 |
| 2016/0303565 A1 * | 10/2016 | Bhagat | .......... | G01N 15/0255 |
| 2017/0296732 A1 * | 10/2017 | Ebrahimi Warkiani | .......... | A61M 1/0281 |

* cited by examiner

*Primary Examiner* — Lore R Jarrett
(74) *Attorney, Agent, or Firm* — Birch, Stewart, Kolasch & Birch, LLP

(57) ABSTRACT

The present invention provides a microfluidic structure for sorting targeted substances. The microfluidic structure includes: an inlet portion having at least one fluid input port; an outlet portion having a plurality of fluid output ports; a first annular flow channel communicated with the inlet portion at the upstream end and rotatably extended; and a second annular flow channel communicated with the downstream end of the first annular flow channel at the upstream end, communicated with the outlet portion at the downstream end and rotatably extended. The first annular flow channel and the second annular flow channel are connected in series according to an S-shaped track, so that the outer side wall of the first annular flow channel is continuously connected to the inner side wall of the second annular flow channel. The cross-sections of the first annular flow channel and the second annular flow channel have a height difference.

16 Claims, 7 Drawing Sheets
(1 of 7 Drawing Sheet(s) Filed in Color)

CASCADED DESIGN MICROFLUIDIC STRUCTURE WITH STEP DIFFERENCE

BACKGROUND OF THE INVENTION

1. Field of the Invention

The present disclosure relates to a microfluidic structure. Specifically, the present disclosure relates to a microfluidic structure with a cascaded design.

2. Description of the Prior Art

Many procedures such as testing, sorting or physical and chemical processing often require complicated procedures to implement. In addition, whether the operation is successful or not highly depends on the experiences and capabilities of the operator. For example, in the medical field, if cancer cells of patients need to be detected, invasive surgeries are often carried out at first so as to obtain cancer cell specimens of patients, and then a test or study is conducted. However, such a method requires much time and effort. It is a heavier burden on the patient's body, and it is impossible to reflect the status of the patient in real time. As such, implementation and development of medicine are therefore limited. However, if an invasive surgery is not conducted to collect Circulating Tumor Cells (CTC) and so on from the blood, it is difficult to collect a large amount of samples enough for treatment or detection due to the small number of CTCs with respect to blood corpuscles or cells and so on.

In view of this, many labs actively develop various types of microfluidic structures using photoresist to conduct optical developing and so on. Microfluidic structures have channels for fluids to pass through, and, depending on the design and characteristics of the channels and the properties and contents of the fluids, expected procedural effects may be produced. Therefore, it is expected that a plurality of originally complicated and difficult procedures of testing, sorting or physical and chemical processing and so on can be realized and popularized by developing and applying the microfluidic structures. In particular, in the medical field that is highly technical and needs to be popularized, it especially needs to develop and study microfluidic structures for various procedures. In addition, the microfluidic structures being developed may also be produced or mass-produced in the form of microfluidic chips and so on so as to reduce the technicality and experience dependency of operating these procedures.

SUMMARY OF THE INVENTION

Technical Method for Solving the Problems

In order to solve the aforementioned problems, the present disclosure provides a microfluidic structure for sorting targeted substances, comprising: an inlet portion having at least one fluid input port; an outlet portion having a plurality of fluid output ports; a first annular flow channel communicated with the inlet portion at the upstream end and rotatably extended; and a second annular flow channel communicated with the downstream end of the first annular flow channel at the upstream end, communicated with the outlet portion at the downstream end and rotatably extended. Wherein the first annular flow channel and the second annular flow channel are connected in series according to an S-shaped track, so that the outer side wall of the first annular flow channel is continuously connected to the inner side wall of the second annular flow channel, and wherein a height difference exists between the cross-sections of the first annular flow channel and the second annular flow channel.

Compared to the Effects in the Prior Art

The microfluidic structure provided by various embodiments according to the present disclosure may sort targeted substances of different sizes in the fluids. Therefore, it is applicable for sorting, collecting or condensing of the specific targeted substances. The microfluidic structure according to the present disclosure, for example, can be applied to the sorting, collecting or condensing of cancer cells which is rarer and has a larger size than the other cells or substances in the blood, so that the status of the patient such as the status of cancer metastasis can be further determined; or it can be applied to the sorting, collecting or condensing of specific pathogens in the lymph so as to detect or determine the infection status of the target object, but not limited thereto.

BRIEF DESCRIPTION OF THE DRAWINGS

The patent or application file contains at least one drawing executed in color. Copies of this patent or patent application publication with color drawing will be provided by the USPTO upon request and payment of the necessary fee.

DETAILED DESCRIPTION OF THE PREFERRED EMBODIMENT

The connecting elements according to the present invention will be described in detail below through embodiments and with reference to the accompanying drawings, a person having ordinary skill in the art may understand the advantages and effects of the present disclosure through the contents disclosed in the present specification. However, the contents shown in the following sentences merely represent examples and never limit the scope of the present disclosure. Therefore, a person having ordinary skill in the present art may easily realize the present disclosure through other embodiments based on different views and applications without departing from the conception principles of the present invention.

Figure 1:
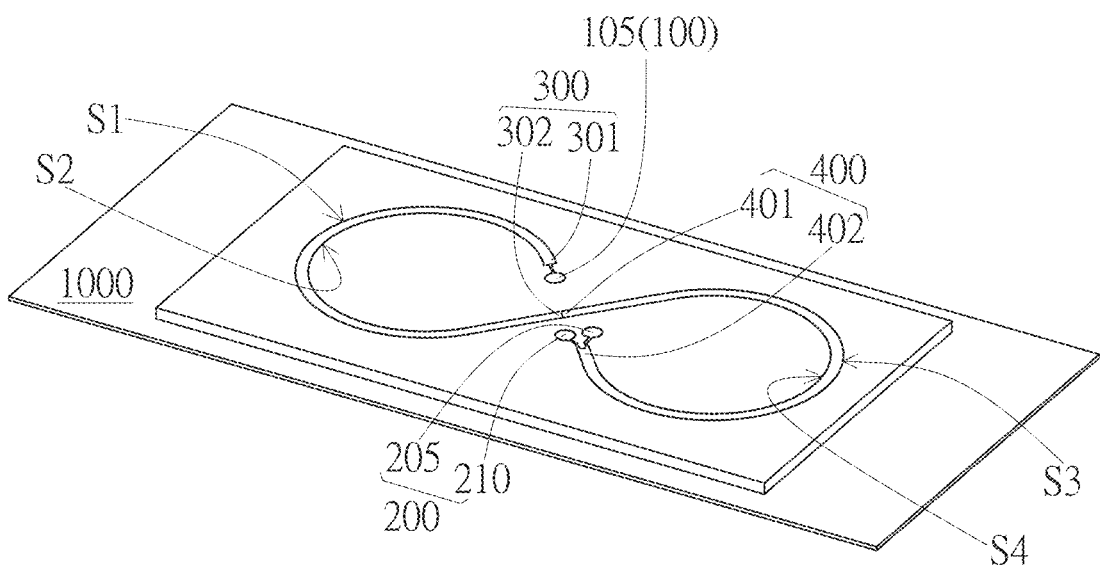
FIG. 1 is a diagram of a microfluidic structure having a height difference in the first embodiment according to the present disclosure.

Please refer to FIG. 1. In the first embodiment according to the present disclosure, a microfluidic structure 10 for sorting targeted substance includes an inlet portion 100, an outlet portion 200, and a first annular flow channel 300 and a second annular flow channel 400 located between the inlet portion 100 and the outlet portion 200. Specifically, the inlet portion 100 may have at least one fluid input port 105 configured to input a test specimen or a pending specimen to the microfluidic structure 10. And the outlet portion 200 may have a plurality of fluid output ports 210 and 205 configured to sort the fluid having different targeted substances or culled matters. Wherein the first annular flow channel 300 is communicated with the inlet portion 100 at the upstream end 301 and extends rotatably. And the second annular flow channel 400 is communicated with the downstream end 302 of the first annular flow channel 300 at the upstream end 401 and communicated with the outlet portion 200 at the downstream end 402 and extends rotatably. Then, according to the present embodiment, the first annular flow channel 300 and the second annular flow channel 400 are connected in series according to an S-shaped track. Based on the structures, the outside wall S1 of the first annular flow channel 300 is connected to the inside wall S4 of the second annular flow channel 400, and the inside wall S2 of the first annular flow channel 300 is connected to the outside wall S3 of the second annular flow channel 400. That is, the outside wall S1 of the first annular flow channel 300 may extend continuously and rotably and turn into the inside wall S4 of the second annular flow channel 400. And the inside wall S2 of the first annular flow channel 300 may extend continuously and rotably and turn into the outside wall S3 of the second annular flow channel 400.

In some embodiments, the maximum radius of the curvatures of the first annular flow channel 300 and the second annular flow channel 400 extending rotatably may range from 0.5 to 2 cm; however, the present disclosure is not limited thereto. For example, the first annular flow channel 300 and the second annular flow channel 400 may respectively form unclosed ring structures and the radius of the curvature can be fixed or changed in the process of rotation, so that the maximum radius of the curvatures may range from 0.5 to 2 cm. According to some embodiments, the first annular flow channel 300 and the second annular flow channel 400 may virtually have the same or similar sizes, radii of the curvatures or processes of changing the curvatures. For example, the first annular flow channel 300 and the second annular flow channel 400 may have a point symmetric structure or rotational symmetric structure based on the junction thereof. However, the present disclosure is not limited thereto. And according to other embodiments, the first annular flow channel 300 and the second annular flow channel 400 may also have different sizes, different radii of the curvatures or different processes of changing the curvatures.

According to the present embodiment, in the microfluidic structure 10, the ring structures of the first annular flow channel 300 and/or the second annular flow channel 400 may have the curvatures configured to generate Dean Vortices in the first annular flow channel 300 and/or the second annular flow channel 400.

In some embodiments, the individual and relative differences of the curvatures of the first annular flow channel 300 and/or the second annular flow channel 400 do not exceed 50%. In some embodiments, the individual and relative differences of the curvatures of the first annular flow channel 300 and/or the second annular flow channel 400 do not exceed 25%. In some embodiments, the individual and relative differences of the curvatures of the first annular flow channel 300 and/or the second annular flow channel 400 do not exceed 15%. In some embodiments, the individual and relative differences of the curvatures of the first annular flow channel 300 and/or the second annular flow channel 400 do not exceed 5%. Therefore, based on the balance between the dean forces and the inertia forces, the sorting properties and the sorting effects can be kept uniform and consistent with respect to the inside and outside walls. In addition, according to some embodiments, the change of the radii of the curvatures of the junction between the first annular flow channel 300 and the second annular flow channel 400 does not exceed 50%, 25%, 15% or 5%. Hence the fluency and stability of the flow of the fluid may be improved when switching the flow channel. However, they merely represent examples, and the present disclosure is not limited thereto.

Figure 2:
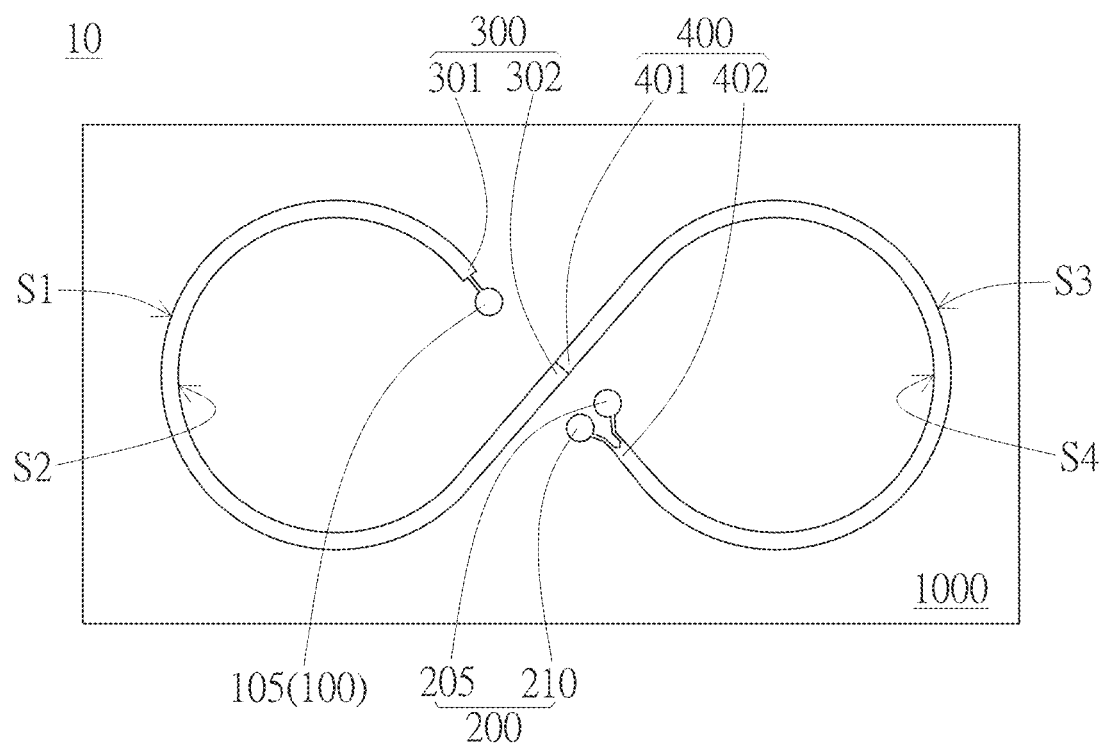
FIG. 2 is the top view of a microfluidic structure having a height difference in the first embodiment according to the present disclosure.
Figure 3:
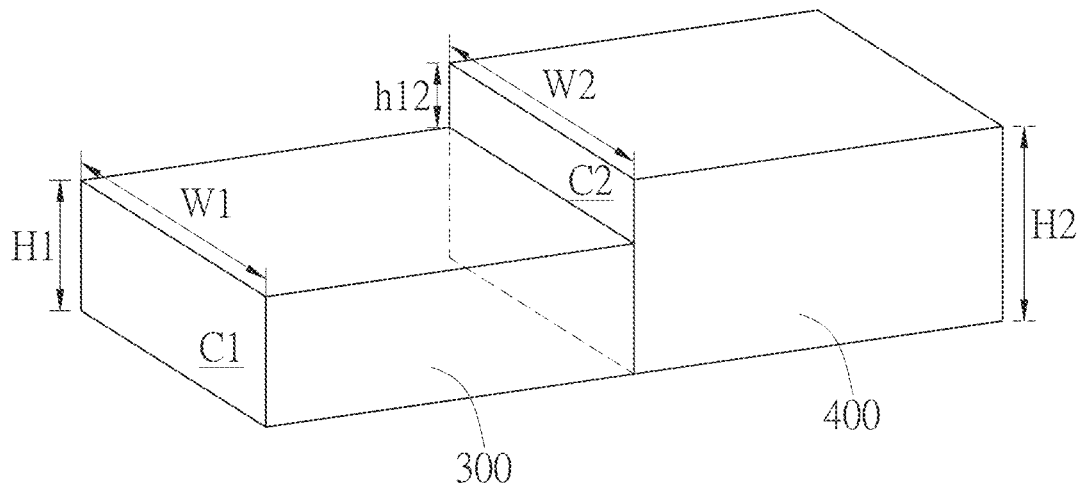
FIG. 3 is a diagram of a microfluidic structure having varied height difference in the first embodiment according to the present disclosure.

Please refer to FIG. 3 together with FIG. 1 and FIG. 2. In the microfluidic structure 10, a height difference may virtually exist between the cross sections C1 of the first annular flow channel 300 and the cross section C2 of the second annular flow channel 400. For example, as shown in FIG. 3, the height H1 of the cross-section C1 of the first annular flow channel 300 may be lower than the height H2 of the cross-section C2 of the second annular flow channel 400. The height difference h12 may exist between the first annular flow channel 300 and the second annular flow channel 400. In some embodiment, the height difference h12 between the cross-section C1 of the first annular flow channel 300 and the cross-section C2 of the second annular flow channel 400 may range from 2 to 200 um. Specifically, in some embodiments, the height difference h12 between the cross-section C1 of the first annular flow channel 300 and the cross-section C2 of the second annular flow channel 400 may range from 5 to 50 um. However, they merely represent examples; and the present disclosure is not limited thereto.

According to some embodiments, the width W1 of the cross-section C1 of the first annular flow channel 300 and the width W2 of the cross-section C2 the second annular flow channel 400 may range from 100 to 1000 um. Wherein the height H1 of the cross-section C1 of the first annular flow channel 300 may range from 20 to 300 um; and the height H2 of the cross-section C2 of the second annular flow channel 400 may range from 30 to 500 um.

The microfluidic structure 10 illustrated in FIG. 1 to FIG. 3, for example, may be formed in a substrate 1000. According to some embodiments, the substrate 1000 may be made of materials such as polydimethylsiloxane (PDMS), polyisoprene, polyethylene terephthalate (PET), glass, quartz and the like; and the present disclosure is not limited thereto. In addition, the channel can be made by ways including but not limited to solid work designs, laser cutting (CNC) and molding by PDMS. Furthermore, the microfluidic structure mentioned above or in the later paragraphs may be manufactured by methods such as drilling and laminating oxygen plasma. However, they merely represent examples. To manufacture the microfluidic structure in each of the embodiment of the present disclosure, the usable manufacturing methods are not limited thereto.

In the microfluidic structure 10 according to the present embodiment, after the fluid is input from the inlet portion 100 to the microfluidic structure 1, the fluid may pass through the first annular flow channel 300 and the second annular flow channel 400 which are communicated with each other in the microfluidic structure 10, so that location differences between each substance in the fluid is gradually generated and the fluids including different substances are respectively sorted in the different fluid output ports 210 and 205 of the outlet portion 200.

Figure 4:
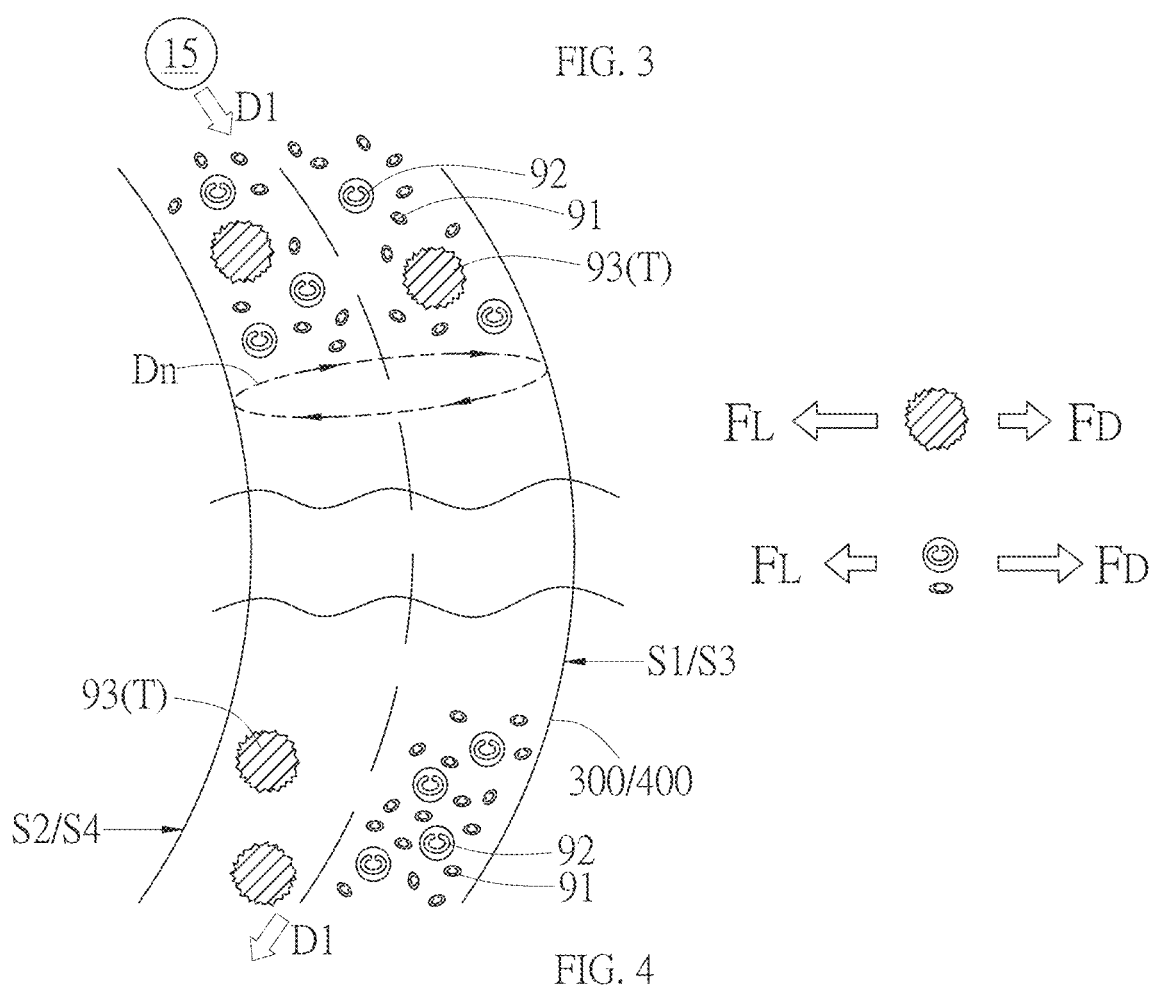
FIG. 4 is a diagram of a microfluidic structure sorting targeted substances in first embodiment according to the present disclosure.

Specifically, according to an embodiment (please refer to FIG. 4), a specimen 15 containing a targeted substance T may be input from the fluid input port (the fluid input port 105 illustrated in FIG. 1 and FIG. 2) to the microfluidic structure 10 of the present embodiment. After the specimen 15 flows along the flowing direction D1, a dean force FD and an inertia force FL may be generated in the first annular flow channel 300 and the second annular flow channel 400 based on a Dean Vortices Dn formed by microscopic characters in the microfluid. Since the dean force FD and the inertia force FL may have different magnitudes or directionalities on the substances of different sizes at the different locations, the different substances will stay at the different locations based on the balancing of the two forces. Specifically, particles with larger sizes may be mainly affected by the inertia force to be deflected to the inside wall of the channel, and particles with smaller sizes may be mainly affected by the dean force to be deflected to the outside wall of the channel. For example, the specimen 15 may be blood, and a large amount of erythrocytes 91, leukocytes 92 and a small amount of cancer cells 93 are included in the blood. Hence the microfluidic structure 10 according to the present embodiment can deflect the cancer cells 93 to the inside wall S2 or S4 and deflect the erythrocytes 91 and the leukocytes 92 to the outside wall S1 or S3 based on the balancing of the dean force FD and the inertia force FL. Therefore, the erythrocytes 91, the leukocytes 92 and the small amount of the cancer cells 93 in the blood can be gradually segmented and sorted by passing through the first annular flow channel 300 and the second annular flow channel 400. Finally, the targeted substance T of the cancer cells 93 which have been concentrated and sorted can be obtained at the output port close to the outlet portion of the inside walls S2 and S4.

In the aforementioned exemplary embodiment, a step difference between the first annular flow channel 300 and the second annular flow channel 400 is kept and the ratios such as aspect ratio can be adjusted in accordance with rules of the dean force FD and the inertia force FL so as to adjust the screening effects on the first annular flow channel 300 and the second annular flow channel 400 respectively. For example, the large amount of the erythrocytes 91 is screened out or eliminated in the first annular flow channel 300 and then, the large amount of the leukocytes 92 can be screened out or eliminated in the second annular flow channel 400 so as to concentrate the cancer cells 93 in the outlet portion 200. However, they merely represent an example; and the present disclosure is not limited thereto.

Then, particle focus parameter can be designed using the aforementioned mechanisms based on the step difference between the first annular flow channel 300 and the second annular flow channel 400 in accordance with the balance and adjustment of the dean force FD and the inertia force FL, so that better sorting efficiency and sorting results can be achieved. In addition, according to some embodiments, the balancing processes can be reinforced repeatedly and by the step difference between the first annular flow channel 300 and the second annular flow channel 400 and the S-shaped series double loop structure thereof. Therefore, the substances which are originally difficult to be sorted in accordance with the balance of the dean force FD and the inertia force FL can be separated indeed. Therefore, the microfluidic structure 10 according to the present embodiment can sort the substances in the fluid with a simple structure and a little pretreatment so as to increase the efficiency and effect of the sorting procedure. Therefore, the microfluidic structure 10 according to the present embodiment may provide easy, rapid and cheap platforms of sorting.

Next, a structure of a microfluidic structure 20 in the second embodiment according to the present disclosure will be described in the contents below with reference to FIG. 5. Most of the details may be identical or similar to the details of the first embodiment illustrated in FIG. 1 to FIG. 4, or at least implemented or formed based on the same principles. Therefore, only a belief description will be mentioned here or the details identical or similar to the aforementioned embodiments will be omitted.

Figure 5:
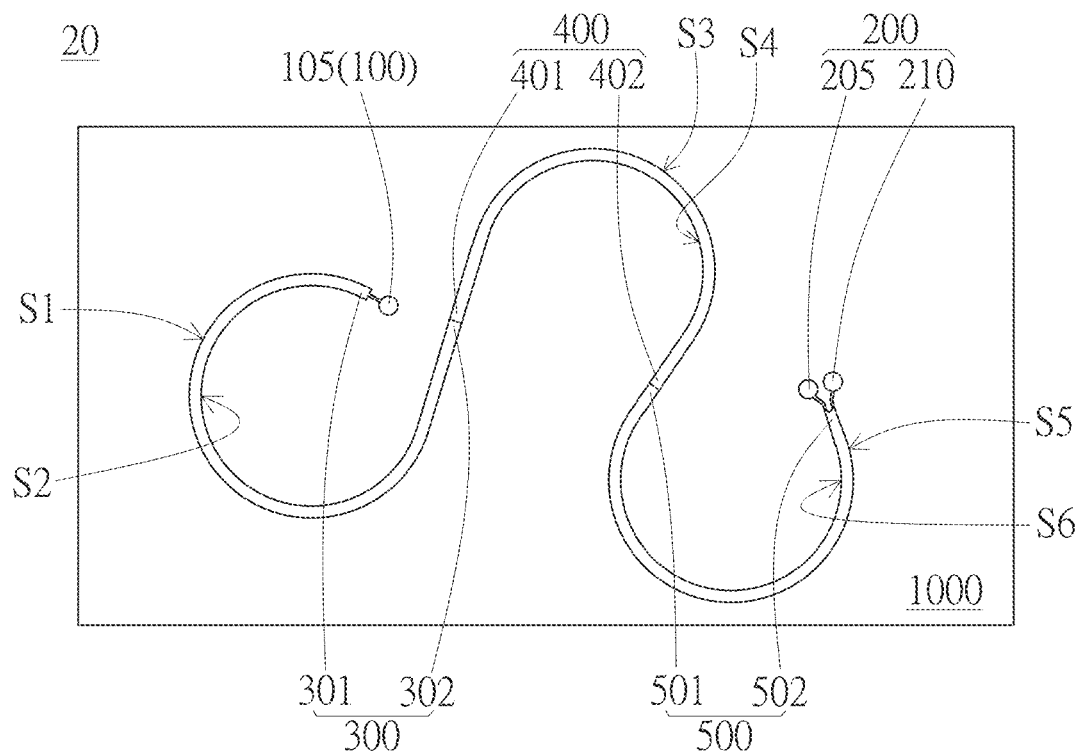
FIG. 5 is the top view of a microfluidic structure having a height difference in the second embodiment according to the present disclosure.

The largest difference between the microfluidic structure 20 in the second embodiment with reference to FIG. 5 and the aforementioned microfluidic structure 10 in the first embodiment is, the former further includes a third annular flow channel 500. Specifically, the second annular flow channel 400 is not directly communicated with the outlet portion 200 but is instead communicated with the outlet portion 200 by connecting to the third annular flow channel 500 in series. The third annular flow channel 500 is communicated with the downstream end 402 of the second annular flow channel 400 at the upstream end 501, and is communicated with the outlet portion 200 at the downstream end 502 to extend rotatably. Similar to the connection in series between the first annular flow channel 300 and the second annular flow channel 400, the second annular flow channel 400 and the third annular flow channel 500 may be connected in series in accordance with the S-shaped track. Therefore, the outside wall S3 of the second annular flow channel 400 may be connected to the inside wall S6 of the third annular flow channel 500, and the inside wall S4 of the second annular flow channel 400 may be connected to the outside wall S5 of the third annular flow channel 500. That is, the outside wall S3 of the second annular flow channel 400 may extend continuously and rotably and turn into the inside wall S6 of the third annular flow channel 500. And the inside wall S4 of the second annular flow channel 400 may extend continuously and rotably and turn into the outside wall S5 of the third annular flow channel 500.

Therefore, by disposing the third annular flow channel 500, the processes of balancing and sorting with reference to FIG. 1 to FIG. 4 may be further repeated. In addition, the size and disposing conditions of the third annular flow channel 500 may be similar or identical to the first annular flow channel 300 and the second annular flow channel 400 described above. A height difference also exists between the third annular flow channel 500 and the second annular flow channel 400. For example, the height difference between the cross-sections of the second annular flow channel 400 and the third annular flow channel 500 may range from 2 to 200 um. In some embodiments, the height difference of the cross-sections between the second annular flow channel 400 and the third annular flow channel 500 may range from 5 to 50 um. Therefore, the balancing of the dean force FD and the inertia force FL may be repeated using the step difference.

And these processes and details are identical or similar to the first embodiment; therefore, they are not described in detail again.

The structure of a microfluidic structure 30 in the third embodiment according to the present disclosure is further described below with reference to FIG. 6. Most of the details may be identical or similar to the details of the first embodiment described with reference to FIG. 1 to FIG. 4 or at least implemented or formed based on the same principles. Therefore, only a belief description will be mentioned here or the details identical or similar to the aforementioned embodiments will be omitted.

Figure 6:
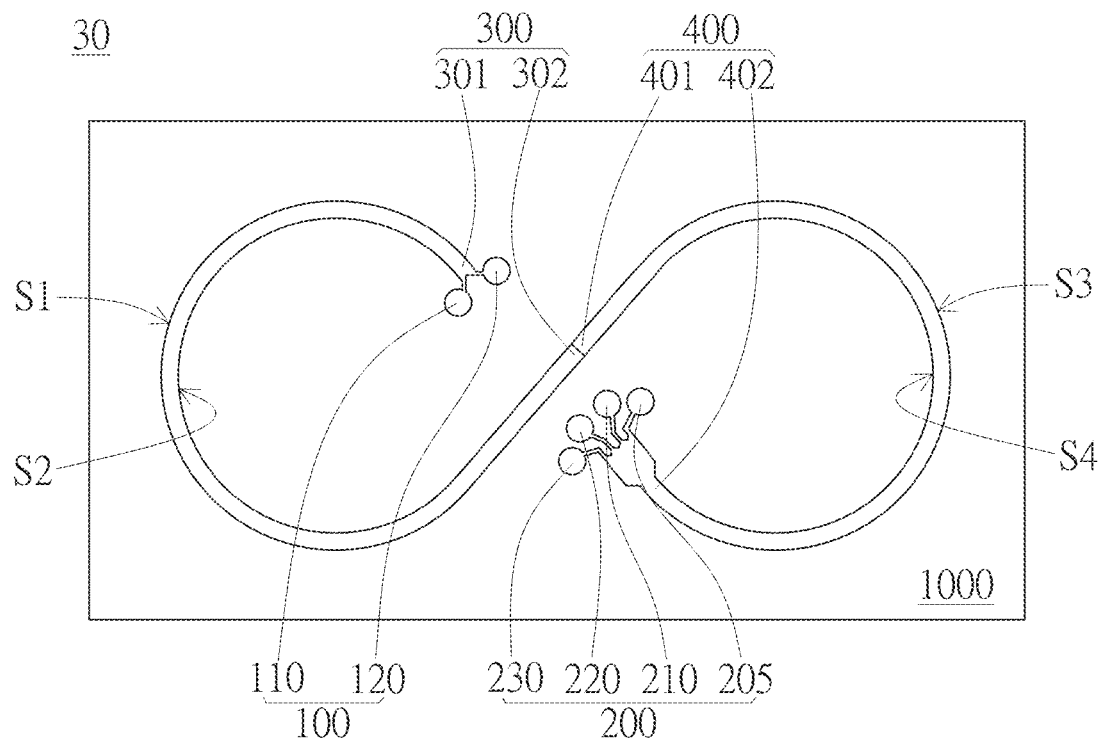
FIG. 6 is the top view of a microfluidic structure having a height difference in the third embodiment according to the present disclosure.

The largest difference between the microfluidic structure 30 in the third embodiment with reference to FIG. 6 and the microfluidic structure 10 in the first embodiment is that at least one fluid input port of the inlet portion 100 includes a specimen input port 10 configured to input the specimen 15 and a buffer solution input port 120 configured to input buffer solution 15'. In addition, at least one fluid output port of the outlet portion 200 may further include a plurality of output ports such as four output ports.

For example, as shown in FIG. 6, the specimen input port 110 may be relatively leaning towards the side of the inside wall S2 of the first annular flow channel 300, and the buffer solution input port 120 may be relatively leaning towards the side of the outside wall S1 of the first annular flow channel 300. However, it merely represents an example, and the present disclosure is not limited thereto. According to other embodiments, the specimen input port 110 may be relatively leaning towards the side of the outside wall S1 of the first annular flow channel 300, and the buffer solution input port 120 may be leaning towards the side of the inside wall S2 of the first annular flow channel 300. In addition, the four output ports may include a targeted substance output port 205 configured to obtain expectedly the targeted substances in the sorting results and at least one distal waste effluent output ports 210, 220 or 230 configured to collect and eliminate the waste effluent.

In the present embodiment, if the size of the targeted substance obtained expectedly range from 10 um to 30 um and is larger than the other substances expected to be eliminated, the targeted substance output port 205, as shown in FIG. 6, may be relatively leaning towards the side of the inside wall S4 of the second annular flow channel 400, and the distal waste effluent output ports 210, 220 and 230 may relatively lean towards the side of the outside wall S3 of the second annular flow channel 400. However, it merely represents an example, and the present disclosure is not limited thereto. For example, according to another embodiment, in the case where the condition of the targeted substances to be screened has been changed, the targeted substance output port 205 may be relatively leaning towards the outside wall S3 of the second annular flow channel 400, and the distal waste effluent output ports 210, 220 and 230 may relatively lean towards the side of the inside wall S4 of the second annular flow channel 400. Or, the targeted substance output port 205 may be any specific one output port among the plurality of output ports between the inside wall S4 of the second annular flow channel 400 and the outside wall S3 of the second annular flow channel 400. The embodiment according to the present disclosure may include various patterns.

The structure of a microfluidic structure 40 in the fourth embodiment according to the present disclosure is described below with reference to FIG. 7. Most of the details are identical or similar to the details of the third embodiment with reference to FIG. 6 or at least implemented or formed based on the same principles. Therefore, only a belief description will be mentioned here or the details identical or similar to the aforementioned embodiments will be omitted.

Figure 7:
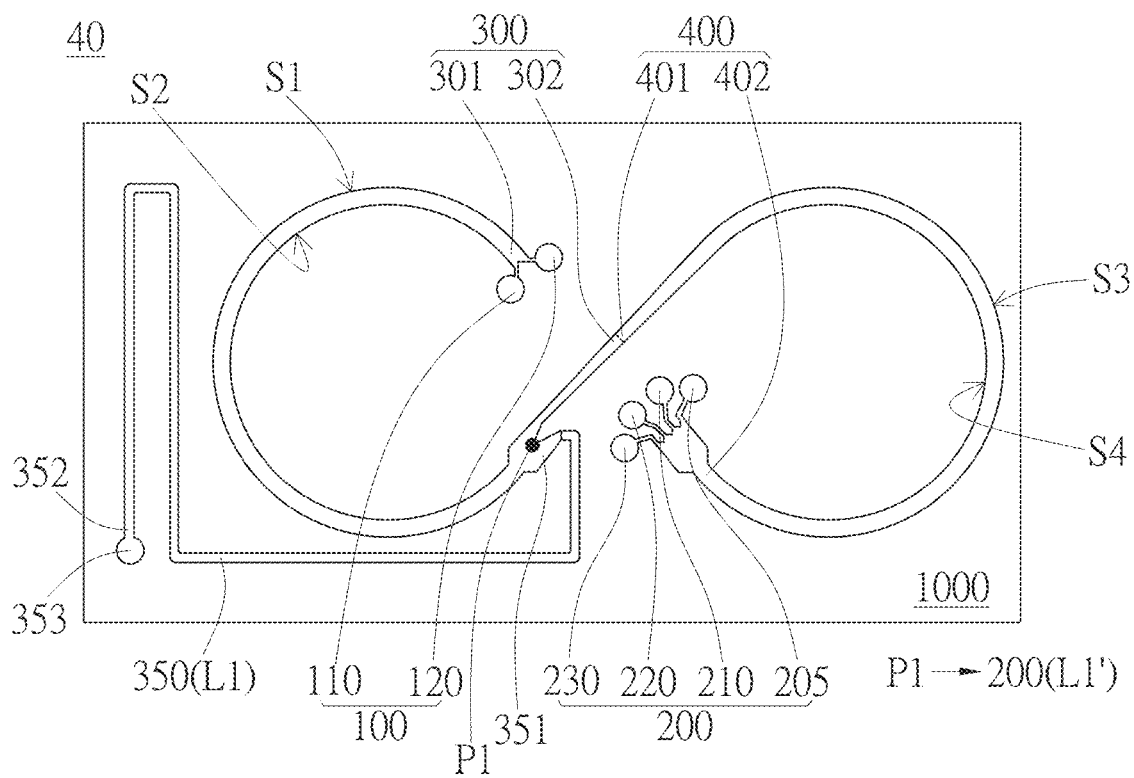
FIG. 7 is the top view of a microfluidic structure having a height difference in the fourth embodiment according to the present disclosure.

The largest difference between the microfluidic structure 40 in the fourth embodiment with reference to FIG. 7 and the microfluidic structure 30 in the third embodiment is, the former further includes a first waste effluent output channel 350. Specifically, the first waste effluent output channel 350 leans towards the side of the outside wall S1 of the first annular flow channel 300 at the upstream end 351 to be communicated with the first annular flow channel 300. For example, the first waste effluent output channel 350 may be leaning towards the side of the outside wall S1 of the first annular flow channel 300 at the latter half section or the distal end of the first annular flow channel 300 to be communicated with the first annular flow channel 300. Therefore, the waste effluent passing through the first annular flow channel 300 and concentrated on the side of the outside wall S1 in preliminary elimination can be exported. For example, the waste effluent can be abandoned after being exported to the first waste effluent output port 353 located at the downstream 352 of the first waste effluent output channel 350. Therefore, the proportion of the targeted substances in the fluid entering the second annular flow channel 400 can be further increased to reduce or prevent the risk and the proportion of the waste effluent being mixed with the targeted substances. However, it merely represents an example. In accordance with the properties of the substance to be eliminated in a different embodiment, the first waste effluent output channel 350 may also be essentially leaning towards the side of the inside wall S2 of the first annular flow channel 300 to be communicated with the first annular flow channel 300, and the concepts can be derived based on the mentioned descriptions and will not be described in detail here.

Furthermore, according to some embodiments, in order to make the fluid flow in the microfluidic structure 40 smoothly (please refer to FIG. 7), if the location at which the first annular flow channel 300 is connected to (communicated with) the first waste effluent output channel 350 is defined to be the bifurcation point P1, the ratio of the length L1 of the first waste effluent output channel 350 and the length L1 extending from the bifurcation point P1 to the outlet portion 200 may range from 0.7 to 1.3. Or, the ratio of the length L1 of the first waste effluent output channel 350 and the length L1 extending from the bifurcation point P1 to the outlet portion 200 may range from 0.8 to 1.2. Or, the length L1 of the first waste effluent output channel 350 and the length L1 extending from the bifurcation point P1 to the outlet portion 200 may range from 0.9 to 1.1. Or, the length L1 of the first waste effluent output channel 350 may be identical to the length L1 extending from the bifurcation point P1 to the outlet portion 200. Therefore, when the fluid arrives at the bifurcation point P1, its resistance to flowing through the first waste effluent output channel 350 can be identical or close to its resistance to flowing through the second annular flow channel 400, so that the fluid can flow to either the first waste effluent output channel 350 or the second annular flow channel 400 more evenly and smoothly depending on its tendency to lean towards the outside wall S1 or the inside wall S2.

Furthermore, the present disclosure can also have at least a portion of the first waste effluent output channel 350 configured to extend rotatably, for example but not limited to, extending rotatably along the side of the outside wall S1 of the first annular flow channel 300 and approximately opposite to the circulation direction of the first annular flow channel 300. Through the rotatable designs, the resistances of the first waste effluent output channel 350 and the second annular flow channel 400 can be identical or similar when the fluid arrives at the bifurcation point P1, so that the sorting effects in accordance with the tendency to lean towards the outside wall S1 or the inside wall S2 are even more significant and smooth.

Next, the structure of a microfluidic structure 50 in the fifth embodiment according to the present disclosure will be further described below with reference to FIG. 8. Most of the details may be identical or similar to the details of the fourth embodiment with reference to FIG. 7 or at least implemented or formed based on the same principles. Therefore, only a belief description will be mentioned here or the details identical or similar to the aforementioned embodiments will be omitted.

Figure 8:
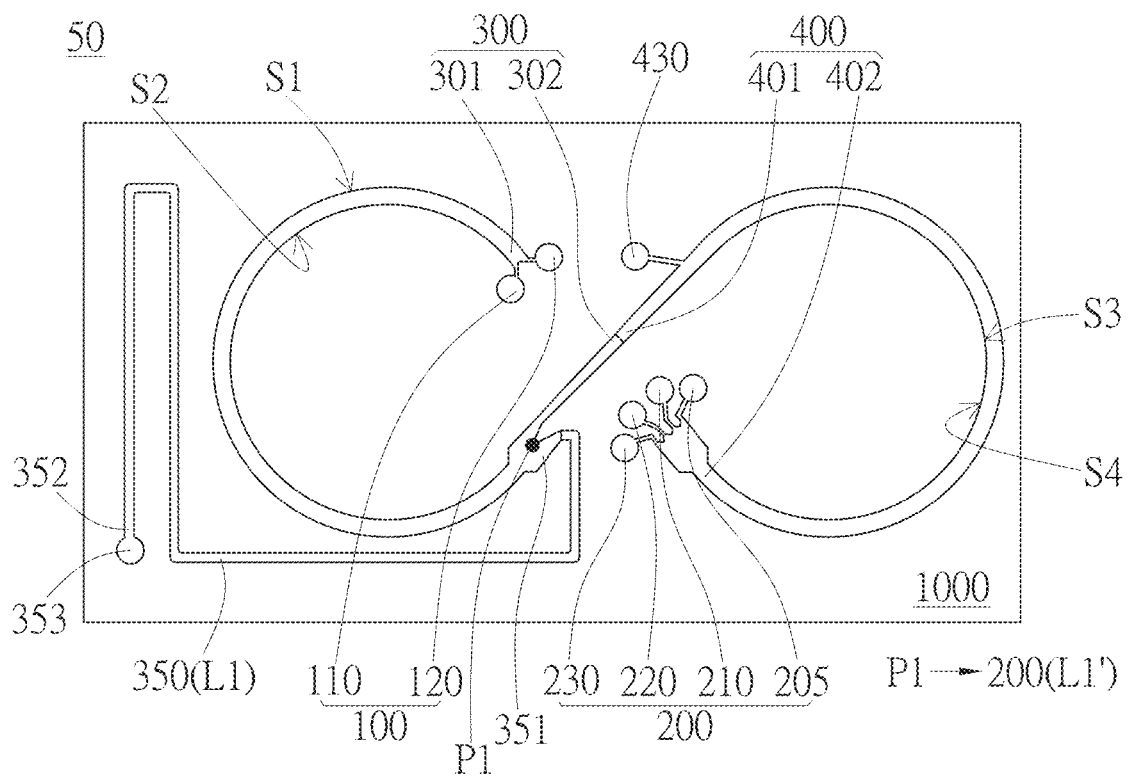
FIG. 8 is the top view of a microfluidic structure having a height difference in the fifth embodiment according to the present disclosure.

The largest difference between the microfluidic structure 50 in the fifth embodiment with reference to FIG. 8 and the microfluidic structure 40 in the fourth embodiment is, the former further includes an intermediate buffer solution input port 430. Specifically, the intermediate buffer solution input port 430 may be communicated with the second annular flow channel 400 at the side of the outside wall S3 of the second annular flow channel 400. Through the structure, the buffer solution lost in the process of screening can be further supplemented so that the circulation of the micro fluid is continued. Or, the content of the buffer solution can be further kept, changed and adjusted in accordance with the properties of the remaining fluids after the waste effluent is eliminated by the first waste effluent output channel 350 and the properties of the targeted substances to be sorted and the remaining impurities so as to enhance the sorting efficiency and effects when the buffer passes through the second annular flow channel 400. In addition, kinetic energy of the fluid flowing through the second annular flow channel 400 can be also provided or the substances can be flushed to the inside wall S4 again so that the dean forces and the inertia forces are balanced again by inputting the buffer solution from the intermediate buffer solution input port 430.

According to another embodiment, in accordance with expected effects such as that the fluid is flushed to the expected outside wall S3 again so that the dean forces and the inertia forces are balanced again and the like, the intermediate buffer solution input port 430 may also be changed to be communicated with the second annular flow channel 400 at the side of the inside wall S4 of the second annular flow channel 400. Or, in accordance with the needed effects and conditions such as the coagulating property or evaporation property of the buffer solution, the intermediate buffer solution input port 430 can also be disposed on any other suitable locations so as to supplement the buffer solution of the microfluidic structure 50 or to provide the kinetic energy for fluid circulation; and the detail will not be described here again.

Figure 9:
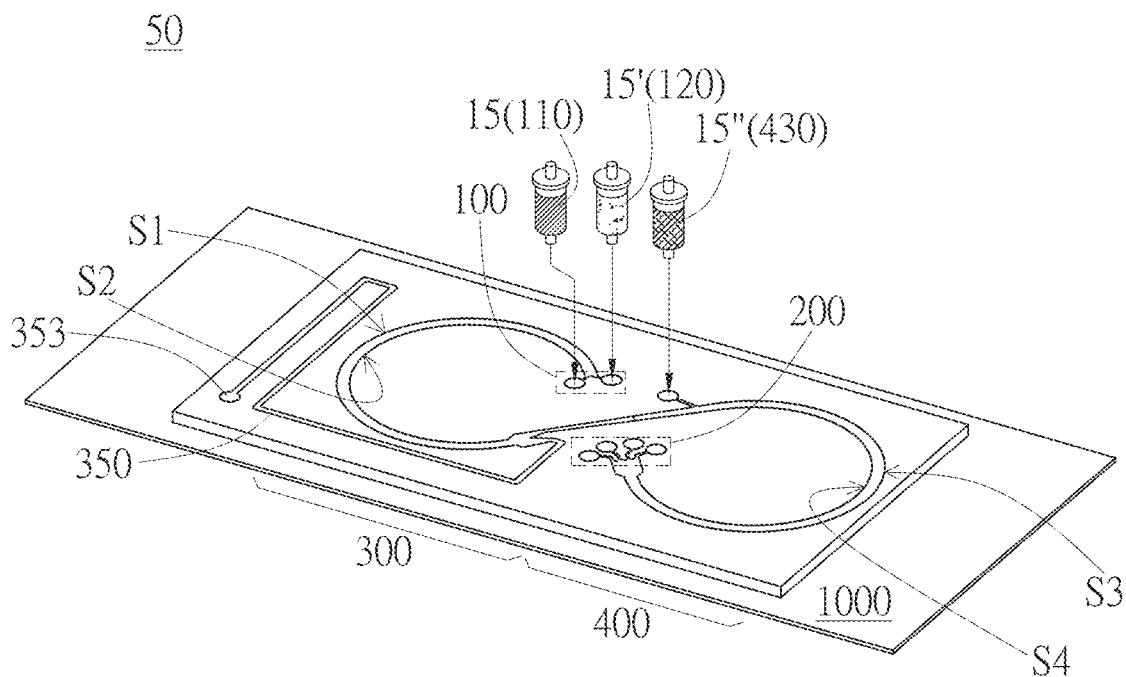
FIG. 9 and FIG. 10 are operational diagrams of processes of sorting targeted substances in the fifth embodiment according to the present disclosure.
Figure 10:
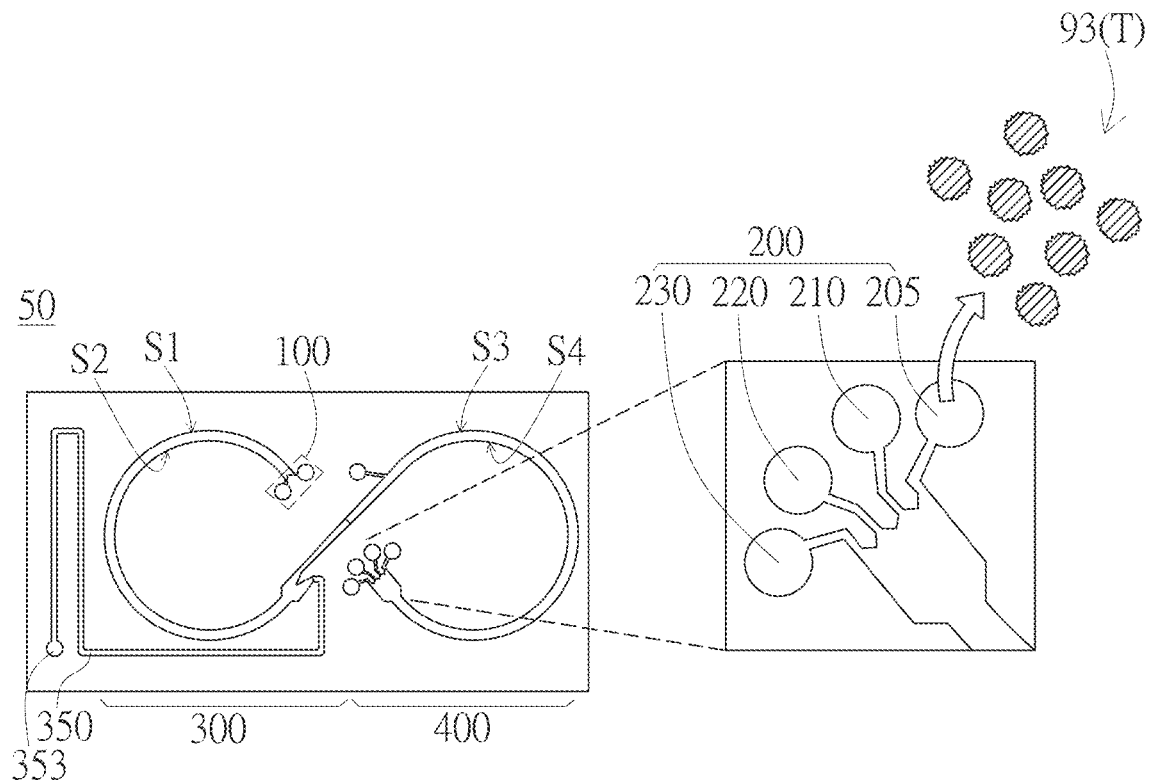

Next, the sorting and collection processes of the microfluidic structure 50 in the fifth embodiment according to the present disclosure will be exemplarily described with references to FIG. 9 and FIG. 10.

According to an embodiment, the specimen 15 which hasn't been sorted or treated yet may be blood, and the dilution level of the whole blood may be smaller than or equal to five-folds, or even smaller than or equal to three-folds. Specifically, the specimen 15 may be whole blood obtained through the standard process of blood collection, and the blood cells, cells, proteins and the like in the same are not artificially destroyed in advance. For example, the specimen 15 is not destroyed by the process of adding a reagent such as an assay buffer. Therefore, the activity, the reliability, and the completeness of the specimen 15 can be kept as much as possible. Therefore, the specimen 15 may accelerate the speed of the sorting, the collection, the concentration and the like using the microfluidic structure 50 by decreasing the dilution level as much as possible (for example, diluted to be lower than or equal to five-folds or three-folds) so as to enhance the efficiency and applicability of the processes of sorting, collection, concentration and the like.

Please refer to FIG. 9. As mentioned above, the specimen 15, for example but not limited thereto, may be inputted to the specimen input port 110 close to the side of the inside wall S2 of the first annular flow channel 300, and buffer solution 15' which helps the circulation of the specimen 15 and does not have destructiveness to the specimen 15 is inputted to the buffer solution input port 120 close to the side of the outside wall S1 of the first annular flow channel 300. Therefore, the specimen 15 mixed with the buffer solution 15' may be guided to be circulated in the microfluidic structure 50.

According to another embodiment, the locations of the specimen input port 110 and the buffer solution input port 120 may be just the opposite of what is shown in FIG. 9. In addition, the specimen 15 may be provided independently without adding the buffer solution 15'. Or, the specimen 15 and the buffer solution 15' may be inputted to the same input port. People skilled in the art should understand these variations of patterns; therefore, the particulars are not described here again.

According to some embodiments, the targeted substance in the specimen 15 may be a substance, biological object, or artificial medical implant expected to be collected whose diameter is larger than 10 um. For example, the specimen 15 may be whole blood, and the targeted substance may be cancer cells whose diameter is larger than 10 um, such as 20 um. Specifically, they may be larger cancer cells which can easily metastasize through blood. Or, when the specimen 15 is whole blood, the targeted substance may be a capsule medicine whose diameter is larger than 10 um, such as 20 um. However, the targeted substance in another embodiment according to the present disclosure is not limited thereto.

As shown in FIG. 9 and FIG. 10, the specimen 15 and the optionally added buffer solution 15' may be circulated through the first annular flow channel 300 and the second annular flow channel 400, so that the sorting can be further conducted by the dean forces and the inertia forces and the step difference between the first annular flow channel 300 and the second annular flow channel 400. Therefore, the cancer cells whose diameter is larger than 10 um such as 20 um may be gradually concentrated on the side(s) of the inside wall S2 and/or the inside wall S4. And the remaining substances such as the erythrocytes whose diameter is approximately 6 um and the leukocyte whose diameter is approximately 10 um may be gradually concentrated on the side(s) of the outside wall S1 and/or the outside wall S3. Then, as shown in FIG. 9, buffer solution 15", which is the same as or different from the buffer solution 15', may be further added or supplemented to the intermediate buffer solution input port 430'. In addition, as shown in FIG. 10, the waste effluent can be eliminated from the first waste effluent output port 353 so as to eliminate the waste effluent preliminarily screened by the first annular flow channel 300 which is close to the side of the outside wall S1. Finally, please refer to FIG. 10. The needed targeted substance T, which is the cancer cells 93 (or any other similar targeted substances), can be obtained from the expected fluid output port 205.

According to an embodiment, tests on the sorting effects with and without step differences may be further conducted similar to the above processes. Specifically, please refer to FIG. 11, wherein the part (a) listed vertically is the test result of the microfluidic structure without step difference (the heights H1' and H2' of the cross-sections C1 and C2 of the first annular flow channel 300 and the second annular flow channel 400 are identical). And the part (b) listed vertically is the test result of the microfluidic structure with step difference (the height H1 of the cross-section C1 of the first annular flow channel 300 is smaller than the height H2 of the cross-section C2 of the second annular flow channel 400). Other than the difference, the structures of the microfluidic structures of part (a) and part (b) shown in FIG. 11 are identical or similar to the microfluidic structure 50 illustrated in FIG. 8.

Figure 11:
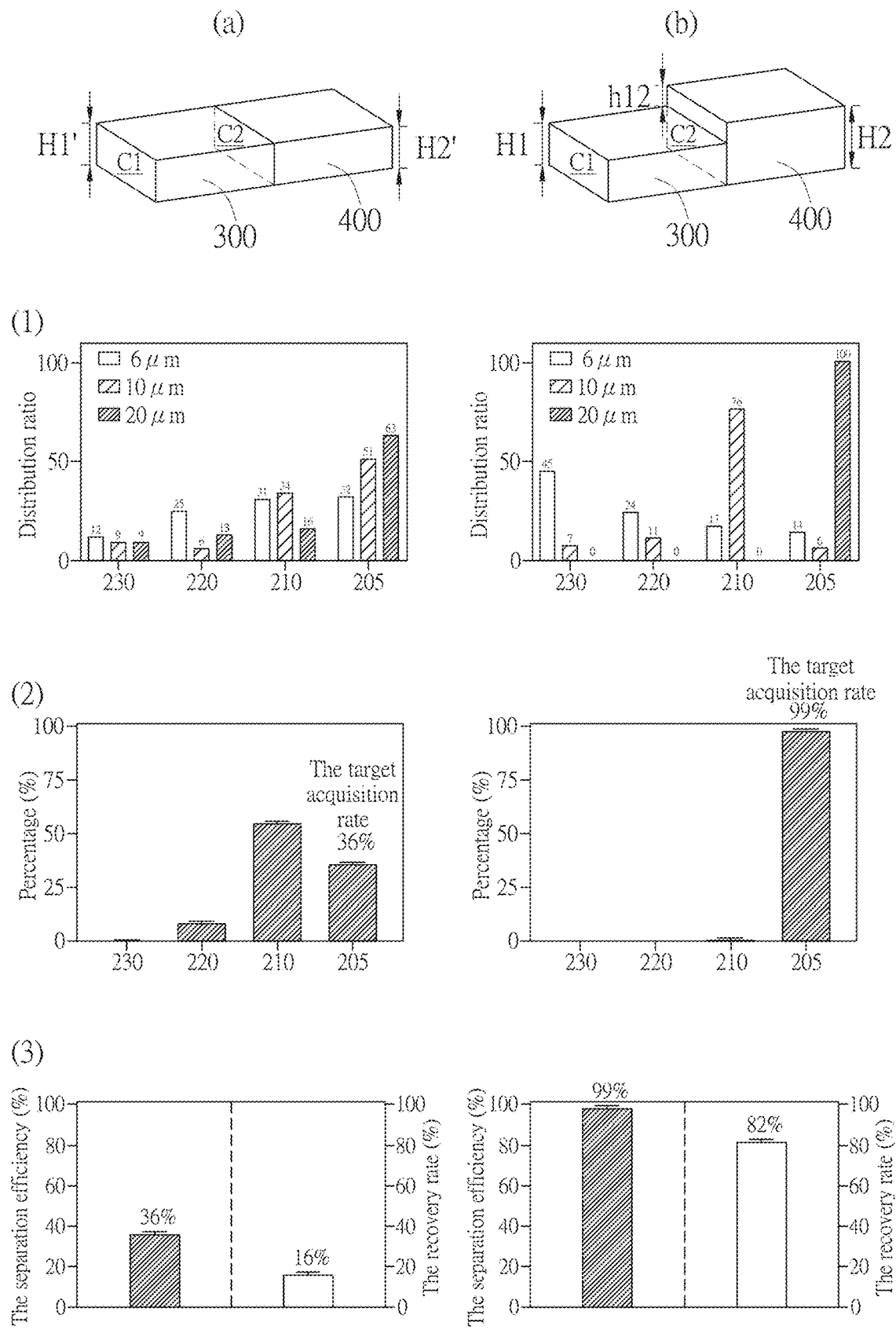
FIG. 11 is a comparison between the experimental result graphs of sorting and collecting by a microfluidic structure having a height difference in the fifth embodiment according to the present disclosure and those by a structure without a height difference.

In an embodiment, the differences caused by whether a step difference exists or not in the structure of the microfluidic structure 50 may be demonstrated using fluorescent ball particles, and the result is shown in part (1) horizontally in FIG. 11. Wherein the fluorescent ball particles whose diameter is 6 um is designed to simulate an erythrocyte, those whose diameter is 10 um is designed to simulate leukocyte, and those whose diameter is 20 um is designed to simulate a cancer cell. Then, in the charts in part (1) of FIG. 11, 6 um represents the distribution ratio of the particles simulating the size of a erythrocyte, 10 um represents that of the particles simulating the size of a leukocyte, and 20 um represents that of the particles simulating the size of a cancer cell. Based on the above conditions and operations and depending on whether the step difference exists or not, we can obtain a relatively more dispersed and mixed distribution of cancer cells in terms of sorting/concentration effect as shown in the part (a) (without step difference) and a relatively simple and consistent distribution of cancer cells in terms of sorting/concentration effect as shown in the part (b) (with step difference).

Based on the above results, the particles simulating erythrocytes and those simulating leukocytes are effectively removed by the output ports 210, 220 and 230 and the large amount of sorted and concentrated particles simulating cancer cells are collected at the output port 205 using the microfluidic structure 50 having a step difference. And in the case of the step difference not existing, it is relatively difficult to separate particles of different sizes.

Next, based on the above result, exemplary tests of the effects of screening real biological samples using the microfluidic structures with and without the step differences are further conducted. Wherein the cancer cells cultured by a cell line of human lung adenocarcinoma cells (A549) are used as a clinical specimen for simulation and confirmation. The actual size of the lung adenocarcinoma cells (A549) is approximately 17 um in average.

Part (2) listed horizontally in FIG. 11 shows the results of the microfluidic structures with and without the step differences sorting the lung adenocarcinoma cells (A549) and collecting them at each of the output ports 205, 210, 220 and 230. Specifically, the predetermined number of the targeted number of cancer cells may be inputted into the microfluidic structure and the cancer cells are collected at the different output ports 205, 210, 220 and 230 so as to calculate the target acquisition rate representing the separation efficiency. The calculation formula is as follows: The separation efficiency (the target acquisition rate)=the number of cancer cells collected at the target output ports/the number of cancer cells collected at all output ports*100%. As a result, as shown in part (a) (without step difference), the separation efficiency (the target acquisition rate) at the output port 205 is approximately only 36% through the screening of the microfluidic structure without step difference. And as shown in part (b) (with the step difference), the separation efficiency (the target acquisition rate) at the output port 205 is very high at approximately 99% through the screening of the microfluidic structure with step difference. The above result further verifies that the microfluidic structure according to the present disclosure can effectively concentrate the cancer cells at the predetermined target output port 205 when a step difference exists between the first annular flow channel 300 and the second annular flow channel 400.

Furthermore, in the same experiment, the recovery rate of the cancer cells may be also calculated. Specifically, the recovery rate=the number of cancer cells at the target output port/the number of cancer cells treated through the microfluidic structure*100%. That is, the rate of cancer cells finally collected at the target output port out of those initially inputted to the whole microfluidic structure may be further calculated. The recovery rate as well as the aforementioned separation efficiency are shown in part (3) horizontally listed in FIG. 11. The result shows that the separation efficiency of the microfluidic structure without step difference, which is shown in part (a), is 36%, and the recovery rate of the same is 16%; the separation efficiency of the microfluidic structure with step difference, which is shown in part (b), is 99%, and the recovery rate of the same is 82%. The above result shows, compared to the microfluidic structure without step difference, for cancer cells as the targeted substance, the microfluidic structure with step difference significantly enhances both the separation efficiency at the different output ports and the recovery rate after inputting the sample.

Finally, clinical sample simulation is further conducted using blood sample in which the aforementioned cancer calls are mixed. Specifically, the specific number of the lung adenocarcinoma cells (A549) may be extracted using a micro extractor and mixed with the blood sample extracted from a healthy body and sorted by a microfluidic structure with step difference the same as the microfluidic structure 50 illustrated in FIG. 8. As such, simulations close to an actual clinical blood sample can be conducted. The sorted cells may be dyed by antibody immunofluorescence which has different expressions of immunofluorescence based on different cells. The effect of sorting is confirmed by detection, for example, using image flow cytometry.

Figure 12:
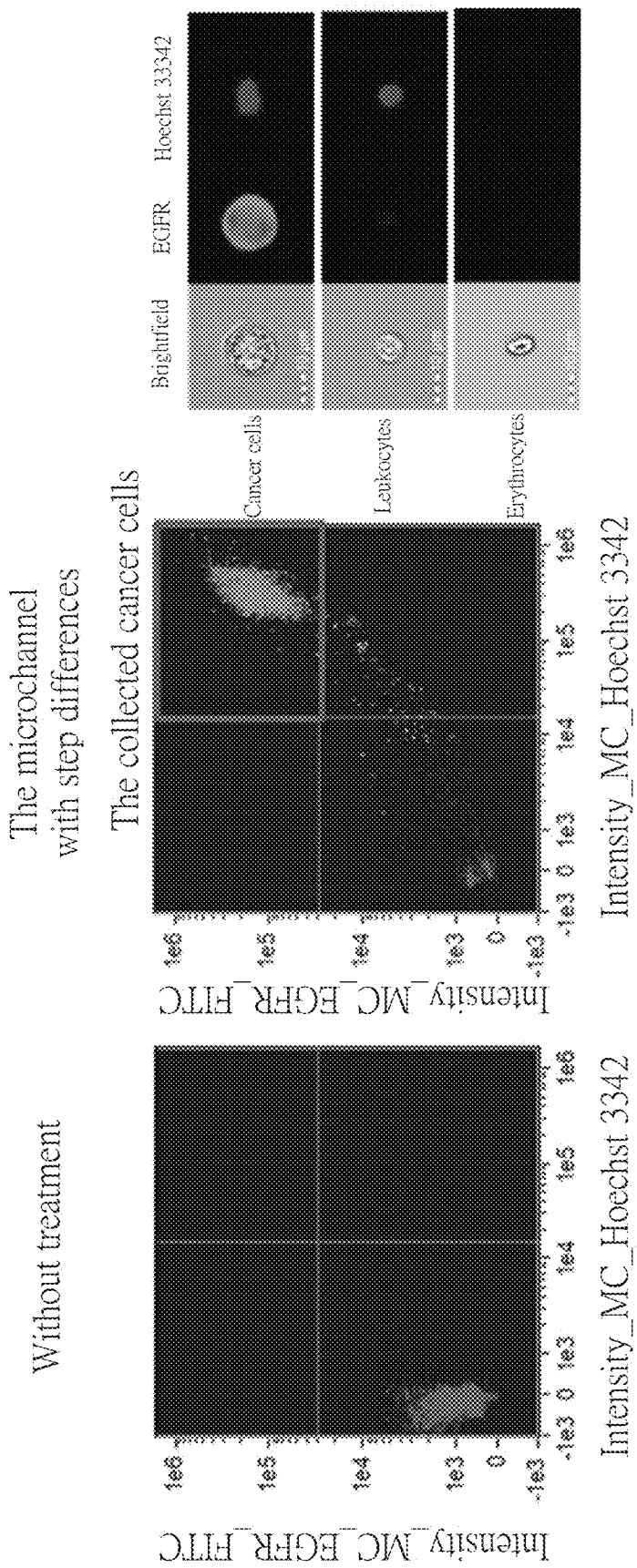
FIG. 12 is an experimental result graph of a microfluidic structure having a height difference in the fifth embodiment according to the present disclosure sorting and collecting cancer cells.

As shown in the result of flow cytometry analysis and cell imaging in FIG. 12, it is observed that the cancer cells (the green block at upper right corner) whose number is originally small in the blood can be significantly collected and concentrated and the interference from the erythrocyte (the red block at lower left corner) whose number is originally large in the blood can be decreased after being treated by the microchannel with step differences. Therefore, the microfluidic structure having a step difference in the various embodiments according to the present disclosure, can significantly enhance the efficiency and the effect of collecting the targeted substance such as cancer cells.

In some embodiments according to the present disclosure, the microfluidic structure may be configured to sort cancer cells whose number is very small in the blood and difficult to collect. In addition, the status of the patient can be determined by further applying procedures such as microscopic examination to the collected cancer cells. Therefore, the status of cancer metastasis of the patient can be discovered at an early stage so as to decrease the burden of invasive surgery on the patient. In addition, the microfluidic structure in each embodiment according to the present disclosure has better efficiency at collecting and concentrating; therefore, it is not required to further add assay buffer to destroy the blood such as blood cells for the effect of having cancer cells. Therefore, if the microfluidic structure in each embodiment according to the present disclosure is applied for sorting cancer cells in the blood, it is further possible to decrease or avoid the reagent such as assay buffer destroying or deforming the targeted cancer cells. Therefore, the activities and properties of the collected cancer cells can be kept and it is more beneficial for the detection or studies at rear end. Therefore, when the microfluidic structure in each embodiment according to the present disclosure is applied to medical procedures, the qualities of the targeted substances after sorting can be kept and enhanced, or pretreatment procedures for specimens or fluid not sorted yet can be reduced or omitted, so that the contents not sorted yet can be kept more intact (for example, using whole blood). However, they merely represent examples. The technical field and the technical scope to which the microfluidic structure of the present disclosure can be applied are not limited thereto.

In addition, cancer cells in the blood can be sorted virtually using the microfluidic structure in each embodiment according to the present disclosure and without using antibodies (antibodies can be used under specific demand, and the present disclosure is not limited thereto). That is, in the case of using the microfluidic structure in the embodiment according to the present disclosure, using antibodies is not a requirement for sorting, and detection using antibodies is merely an additional procedure for optionally confirming the sorting effect.

In a microfluidic structure in some embodiments according to the present disclosure, the fluence of the sorted blood may be 0.25 mL/min. In some embodiments according to the present disclosure, the concentration rate of the targeted substance may be larger than 1000-folds at most. For example, in a different embodiment according to the present disclosure, the concentration rate of the targeted substance may be 1000-folds, 2000-folds, 3000-folds, 4000-folds, 5000-folds, 6000-folds, 7000-folds, 8000-folds, 9000-folds, and even 10000-folds. For example, according to the pattern of the microfluidic structure 50 with step difference as shown in FIG. 8, regarding the blood sample made by mixing the cultured A549 cancer cells and blood extracted from a healthy human and dilute at 5-folds, when the injection speed inputting the sample into the channel is as follows: 0.4 m/s for the blood sample, 0.9 m/s for the first phase solution (the buffer solution inputted from the inlet portion; the phosphate buffered saline (PBS) is used here), and 0.7 m/s for the second phase buffer solution (the buffer solution inputted from the intermediate buffer solution input port; the phosphate buffered saline (PBS) is used here), 7.5 ml of sample can be treated within 2.5 hours, and the liquid that is finally collected (obtained at the output port 205) may achieve 10000-folds concentration effect to the A549 cancer cells at the most with respect to the concentration of the original blood sample.

The phosphate buffered saline (PBS) used in the above embodiment, whose osmotic pressure and ionic concentration are known to match the human body, can be used as the buffer solution in the present embodiment. The aforementioned PBS will never virtually destroy substances such as blood cells or other cells in the blood sample and won't virtually change the properties of substances such as blood cells or other cells to keep certain activity level of the substances such as blood cells or other cells. However, it merely represents an example and the buffer solution usable in the present disclosure is not limited thereto. For example, when the above conditions are satisfied, any known buffer solution or buffer solution developed in the future can be used.

Therefore, using the microfluidic structure in each embodiment according to the present disclosure, 1000 to 10000-folds concentrating effect on the targeted substance can be achieved. Therefore, for example, it is applicable to preconcentration procedures before conducting many types of detection procedures; and the applicable procedure is not limited thereto.

In summary, the microfluidic structure in each embodiment according to the present disclosure can sort substances of different sizes in a fluid based on channel structures communicated simply and repeatedly or continuously, and obtain substances of different sizes after sorting and concentrating. Therefore, the microfluidic structure in each embodiment according to the present disclosure is applicable to simplifying and improving many complicated or difficult procedures so as to improve and enhance the efficiency of sorting and the level of the concentration.

The mentioned contents merely represent some better mode embodiments of the present disclosure. Please note that various changes and modifications of the present disclosure are allowed without departing from the conception principles of the present invention. People skilled in the art should understand that the scope of the present disclosure are defined by claims, and various replacements, combinations, modifications, and shifting based on intention of the present disclosure are all viewed as being embraced by the scope of the present disclosure.

What is claimed is:

1. A microfluidic structure for sorting targeted substances, comprising:
   an inlet portion having at least one fluid input port;
   an outlet portion having a plurality of fluid output ports;
   a first annular flow channel communicated with the inlet portion at an upstream end and extending rotatably; and
   a second annular flow channel communicated with a downstream end of the first annular flow channel at the upstream end, communicated with the outlet portion at a downstream end and extending rotatably,
   wherein the first annular flow channel and the second annular flow channel are connected in series according to an S-shaped track, so that an outer side wall of the first annular flow channel is continuously connected to an inner side wall of the second annular flow channel, and
   wherein a height of cross-section of the first annular flow channel is lower than a height of cross-section of the second annular flow channel.

2. The microfluidic structure according to claim 1, wherein the height difference between the cross-sections of the first annular flow channel and the second annular flow channel ranges from 2 to 200 um.

3. The microfluidic structure according to claim 2, wherein the height difference between the cross-sections of the first annular flow channel and the second annular flow channel ranges from 5 to 50 um.

4. The microfluidic structure according to claim 1, further comprising a third annular flow channel, the third annular flow channel communicated with the downstream end of the second annular flow channel at an upstream end, communicated with the outlet portion at a downstream end, and extending rotatably,
wherein the second annular flow channel and the third annular flow channel are connected in series according to an S-shaped track, so that an outer side wall of the second annular flow channel is continuously connected to an inner side wall of the third annular flow channel.

5. The microfluidic structure according to claim 1, wherein the at least one fluid input port is configured to input a specimen having a subject matter.

6. The microfluidic structure according to claim 5, wherein the specimen is whole blood.

7. The microfluidic structure according to claim 5, wherein a diameter of the subject matter is larger than 10 um.

8. The microfluidic structure according to claim 5, wherein the subject matter is a cancer cell.

9. The microfluidic structure according to claim 5, wherein the at least one fluid input port includes a specimen input port for inputting the specimen, and a buffer solution input port for inputting a buffer solution, and
wherein the specimen input port is closer to an inner side wall of the first annular flow channel compared to the buffer solution input port, and the buffer solution input port is closer to an outer side wall of the first annular flow channel compared to the specimen input port.

10. The microfluidic structure according to claim 1, wherein the plurality of fluid output ports include a subject matter output port, and at least one distal waste effluent output port, and
wherein the subject matter output port is leaned to an inner side wall of the second annular flow channel with respect to the at least one distal waste effluent output port.

11. The microfluidic structure according to claim 1, further comprising a first waste effluent output flow through, the first waste effluent output flow through is communicated with the first annular flow channel at an outer side wall of a second half of the first annular flow channel at upstream end.

12. The microfluidic structure according to claim 11, wherein when a portion of the first annular flow channel connected to the first waste effluent output flow through is defined as a bifurcation point, a rate of a length of the first waste effluent output flow through to a length extending from the bifurcation point to the outlet portion ranges from 0.7 to 1.3.

13. The microfluidic structure according to claim 11, wherein at least a portion of the first waste effluent output flow through extends rotatably.

14. The microfluidic structure according to claim 1, further comprising an intermedium buffer solution input portion, wherein the intermedium buffer solution input portion is communicated with the second annular flow channel at an outer side wall of a first half of the second annular flow channel.

15. The microfluidic structure according to claim 1, wherein maximum radius of curvatures of the first annular flow channel and the second annular flow channel extending rotatably range from 0.5 to 2 cm.

16. The microfluidic structure according to claim 1, wherein widths of cross-sections of the first annular flow channel and the second annular flow channel range from 100 to 1000 um, and
wherein a height of a cross-section of the first annular flow channel ranges from 20 to 300 um, and a height of a cross-section of the second annular flow channel ranges from 30 to 500 um.

\* \* \* \* \*